United States Patent
Schneider et al.

(10) Patent No.: US 7,400,107 B2
(45) Date of Patent: Jul. 15, 2008

(54) SURGICAL MACHINE AND METHOD FOR OPERATING A SURGICAL MACHINE

(75) Inventors: Juergen Schneider, Tuttlingen (DE); Roland Alois Hoegerle, Tuttlingen (DE); Harald Konrath, Rottenburg-Hailfingen (DE)

(73) Assignee: AESCULAP AG & Co. KG, Tuttlingen (DE)

( * ) Notice: Subject to any disclaimer, the term of this patent is extended or adjusted under 35 U.S.C. 154(b) by 0 days.

(21) Appl. No.: 11/645,237

(22) Filed: Dec. 21, 2006

(65) Prior Publication Data

US 2007/0147806 A1    Jun. 28, 2007

Related U.S. Application Data

(63) Continuation of application No. PCT/EP2005/007760, filed on Jul. 16, 2005.

(30) Foreign Application Priority Data

Jul. 30, 2004    (DE) .................. 10 2004 038 414

(51) Int. Cl.
*H02K 17/32*    (2006.01)

(52) U.S. Cl. .................. 318/434; 318/471; 318/432; 318/254

(58) Field of Classification Search .................. 318/434, 318/471, 432, 254, 138, 439; 388/934, 930
See application file for complete search history.

(56) References Cited

U.S. PATENT DOCUMENTS 2,244,683 A    6/1941    Fisher (Continued)

FOREIGN PATENT DOCUMENTS

DE    80 00 592    4/1980

(Continued)

OTHER PUBLICATIONS

Ying-Yu Tzou, et al., "FPGA-Based SVPWM Control IC for 3-Phase PWM Inverters" Proceedings of the 22nd International Conference on Industrial Electronics, Control and Instrumentation, Aug. 1996, pp. 138-143 (XP002360956).

(Continued)

*Primary Examiner*—Karen Masih
(74) *Attorney, Agent, or Firm*—Lipsitz & McAllister, LLC

(57) ABSTRACT

To improve a surgical machine with an electric motor comprising a rotor and a plurality of motor windings, and with a motor controller for controlling and/or regulating the electric motor so that, in particular, the efficiency of the electric motor can be optimized essentially over the entire rotational speed range, it is proposed that the entire rotational speed range of the surgical machine be divided into at least one lower rotational speed range for low rotational speeds and at least one upper rotational speed range for higher rotational speeds than those in the at least one lower rotational speed range, that the motor controller be so designed that a first controlling and/or regulating method for controlling and/or regulating the electric motor is performable in the at least one lower rotational speed range, and that a second controlling and/or regulating method for controlling and/or regulating the electric motor is performable in the at least one upper rotational speed range.

24 Claims, 2 Drawing Sheets

U.S. PATENT DOCUMENTS

Figure 1:
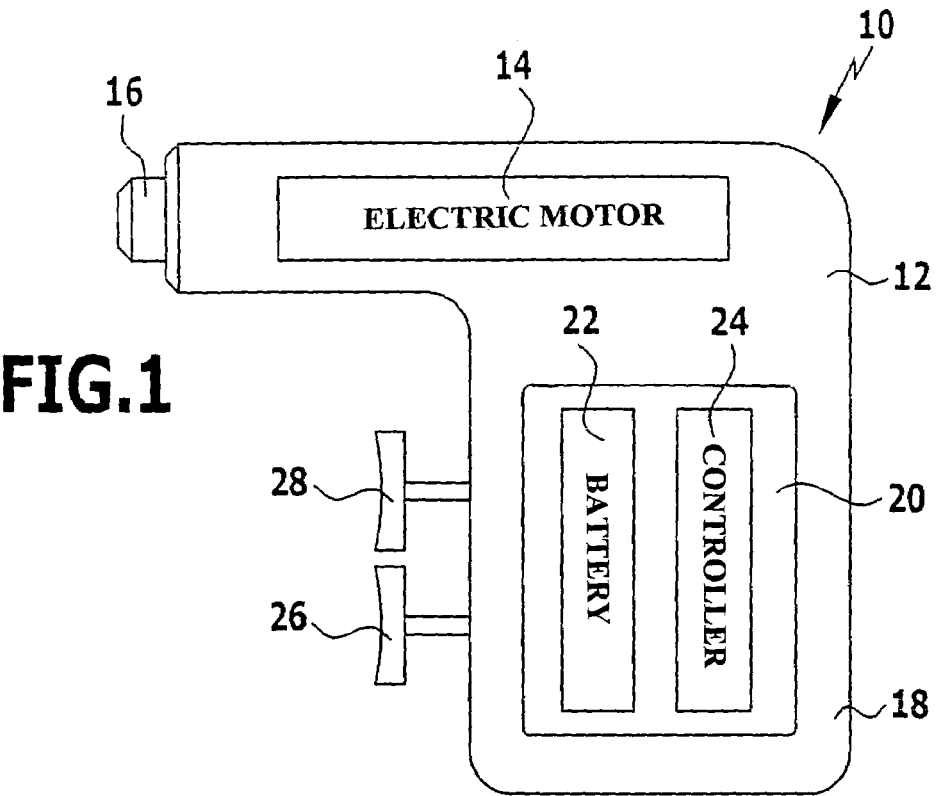

| | | |
|---|---|---|
| 4,091,880 A | 5/1978 | Troutner et al. |
| 5,107,151 A | 4/1992 | Cambier |
| 5,268,622 A | 12/1993 | Philipp |
| 5,677,605 A | 10/1997 | Cambier et al. |
| 5,689,159 A | 11/1997 | Culp et al. |
| 5,747,953 A | 5/1998 | Philipp |
| 5,994,867 A | 11/1999 | Birk et al. |
| 6,013,991 A | 1/2000 | Philipp |
| 6,059,806 A | 5/2000 | Hoegerle |
| 6,086,544 A | 7/2000 | Hibner et al. |
| 6,249,094 B1 | 6/2001 | Zeh et al. |
| 6,643,149 B2 | 11/2003 | Arnet et al. |
| 6,819,078 B2 | 11/2004 | Ho |
| 6,885,163 B2 | 4/2005 | Heidrich |
| 2002/0044472 A1 | 4/2002 | Arnet et al. |
| 2003/0155878 A1 | 8/2003 | Murai |
| 2006/0071541 A1* | 4/2006 | Berg .......................... 303/89 |
| 2006/0119305 A1 | 6/2006 | Lee et al. |

FOREIGN PATENT DOCUMENTS

| | | |
|---|---|---|
| DE | 198 46 831 | 4/2000 |
| DE | 202 02 724 | 6/2002 |
| DE | 20 2004 006 724 | 7/2004 |
| DE | 10 2004 020 808 | 11/2005 |
| WO | 96/01521 | 1/1996 |
| WO | 97/50171 | 12/1997 |
| WO | 98/06338 | 2/1998 |
| WO | 03/052919 | 6/2003 |
| WO | 2004/036755 | 4/2004 |

OTHER PUBLICATIONS

Felix Jenny/Dieter Wüest, "Steuerverfahren für selbstgeführte Stromrichter", 1995 vdf Hochschulverlag AG and der ETH Zürich and B.G Teubner Stuttgart (10 pages).

* cited by examiner

SURGICAL MACHINE AND METHOD FOR OPERATING A SURGICAL MACHINE

This application is a continuation of international application number PCT/EP2005/007760 filed on Jul. 16, 2005.

The present disclosure relates to the subject matter disclosed in international application number PCT/EP2005/007760 of Jul. 16, 2005 and German application number 10 2004 038 414.2 of Jul. 30, 2004, which are incorporated herein by reference in their entirety and for all purposes.

BACKGROUND OF THE INVENTION

The present invention relates to a surgical machine with an electric motor comprising a rotor and at least two motor windings, and with a motor controller for controlling and/or regulating the electric motor.

The present invention further relates to a method for operating a surgical machine with an electric motor comprising a rotor and at least two motor windings, and with a motor controller for controlling and/or regulating the electric motor.

Surgical machines of the kind described at the outset are known in a multitude of variants, especially as drilling and milling machines or saws. They are operated by control signals being generated by the motor controller for the electric motor in order to operate it at a certain rotational speed. Depending on the type of electric motor, rotational speeds of up to 70,000 revolutions per minute can be reached. Due to the construction, however, the efficiency of electric motors is not identical, and, in particular, not always optimal, at all rotational speeds.

The object of the present invention is, therefore, to so improve a surgical machine and a method for operating a surgical machine that, in particular, the efficiency of the electric motor can be optimized essentially over the entire rotational speed range.

SUMMARY OF THE INVENTION

This object is accomplished with a surgical machine of the kind described at the outset, in accordance with the invention, in that the entire rotational speed range of the surgical machine is divided into at least one lower rotational speed range for low rotational speeds and at least one upper rotational speed range for higher rotational speeds than those in the at least one lower rotational speed range, in that the motor controller is so designed that a first controlling and/or regulating method for controlling and/or regulating the electric motor is performable in the at least one lower rotational speed range, and in that a second controlling and/or regulating method for controlling and/or regulating the electric motor is performable in the at least one upper rotational speed range.

The further development, in accordance with the invention, of known surgical machines has the advantage that controlling and/or regulating methods that are respectively adapted to a rotational speed range of the electric motor can be employed. In particular, it is conceivable for more than two rotational speed ranges to be defined, and for the respectively used controlling and/or regulating method to also be switched over at the respective transition from one rotational speed range to the other. In this way, not only the efficiency of the electric motor can be optimized during operation, but, for example, an actual rotational speed of the electric motor during operation can also be determined in an optimized manner in dependence upon the rotational speed.

It is advantageous for the first and/or the second controlling and/or regulating method to be a pulse width modulation (PWM) method. In particular, DC motors can be operated in a simple and optimized manner with this method. In particular, sinusoidal current and voltage courses can be generated by superposing a carrier frequency on digital voltage or current signals.

In accordance with a preferred embodiment of the invention it may be provided for the first controlling and/or regulating method to be a space vector pulse width modulation (SVPWM) method in which all motor windings are able to be simultaneously supplied with electric current. The SVPWM method has the advantage over conventional pulse width modulation (PWM) methods that all motor windings are able to be simultaneously supplied with electric current, so that a smooth, jerk-free operation of the electric motor is also possible at particularly low rotational speeds. Furthermore, starting of the motor from a standstill is considerably improved by all motor windings being able to be simultaneously supplied with electric current.

The machine is particularly cost-effective and requires less intensive maintenance when the electric motor is a brushless DC motor.

The electric motor is preferably a sensorless electric motor. This means that no rotational speed detection sensors for determining an actual rotational speed of the electric motor are provided or arranged on the electric motor. Such electric motors are considerably more cost-effective than motors comprising sensors, and, in addition, the overall construction of the surgical machine is simplified. This is due to fewer connections having to be provided for the motor. This also has the advantage that in the case of a surgical machine that can be disassembled no corrosion problems can occur with contacts for connecting the motor controller to rotational speed detection sensors and/or position sensors. Small voltages or currents are usually applied to such contacts, and so even a slight corrosion of the contacts may result in errors in the determination of the actual rotational speed of the electric motor. Precisely this cannot occur with a machine according to the invention.

Alternatively, it may be provided in an advantageous manner for the motor to comprise rotational speed detection sensors and for the motor controller to be so designed that the first controlling and/or regulating method is a method for controlling and/or regulating the surgical machine, in which the motor controller provides control signals for the electric motor in dependence upon an actual rotational speed determined with the rotational speed detection sensors. The rotational speed detection sensors may also serve to determine a position of the rotor of the electric motor. Use of rotational speed detection sensors, in particular, at low rotational speeds of the electric motor has the advantage that the rotational speed can be determined considerably more precisely than, for example, by determining a CEMF (counterelectromotive force) generated at the motor winding or windings. In particular, the determination of the CEMF (counterelectromotive force) is more suitable at higher rotational speeds, as higher induction voltages are generated, in this case, and the detected signals can therefore be processed better.

A particularly simple construction of the machine is obtained when a Hall system is provided for detecting an actual rotational speed of the electric motor and when the Hall system comprises the rotational speed detection sensors. Hall sensors as rotational speed detection sensors can be made particularly small and integrated directly into the electric motor.

In accordance with a preferred embodiment of the invention it may be provided that a rotational speed limit value between the at least one lower rotational speed range and the at least one upper rotational speed range is unalterable. In this case, a switchover between the at least two controlling and/or regulating methods can always take place at a desired rotational speed limit value.

In accordance with a further preferred embodiment of the invention it may also be provided that a rotational speed limit value between the at least one lower rotational speed range and the at least one upper rotational speed range is alterable. Depending on the operating situation, it is thus possible to specifically alter a switchover between the at least two controlling and/or regulating methods. Switching points can then be varied in a desired manner.

A constant switching-over between the at least two controlling and/or regulating methods can be avoided in a simple way by the motor controller being so designed that a switchover from the first controlling and/or regulating method to the second controlling and/or regulating method takes place at a first switchover rotational speed and a switchover from the second controlling and/or regulating method to the first controlling and/or regulating method takes place at a second switchover rotational speed. Two switching points can thus be defined, namely at the transition from the lower rotational speed range to the higher rotational speed range, and vice versa. It is thus possible to separate the switchover times, i.e., a small variation in the actual rotational speed of the motor does not necessarily immediately result in a switchover to the other controlling and/or regulating method.

In principle, it is conceivable for the first switchover rotational speed to be less than the second switchover rotational speed. It is, however, particularly expedient for the first switchover rotational speed to be equal to or greater than the second switchover rotational speed. A switchover to the higher rotational speed range therefore takes place at a higher switchover rotational speed than the switchover from the higher rotational speed range to the lower rotational speed range. This therefore results in a hysteresis curve, as it were, with a range in which both the one and the other controlling and/or regulating methods are used for certain rotational speeds, but in dependence upon whether the rotational speed of the electric motor increases or decreases.

In principle, it would be possible to so design the machine that an operator specifies a desired rotational speed range and activates the corresponding controlling and/or regulating method. In accordance with a preferred embodiment of the invention it may, however, be provided that the motor controller is so designed that the switchover from the first controlling and/or regulating method to the second controlling and/or regulating method takes places automatically at the transition from the at least one lower rotational speed range to the at least one upper rotational speed range, and vice versa. With this inventive design of the machine, the operator need only specify the rotational speed at which the machine is to operate.

The construction of the machine becomes particularly simple when the electric motor comprises three motor windings. Such electric motors are available in a multitude of constructional variants and, in particular, also cost-effective ones.

The object set at the outset is accomplished in a method of the kind described at the outset, in accordance with the invention, in that the entire rotational speed range of the surgical machine is divided into at least one lower rotational speed range for low rotational speeds and at least one upper rotational speed range for higher rotational speeds than those in the at least one lower rotational speed range, in that a first controlling and/or regulating method for controlling and/or regulating the electric motor is performed in the at least one lower rotational speed range, and in that a second controlling and/or regulating method for controlling and/or regulating the electric motor is performed in the at least one upper rotational speed range.

A surgical machine can be advantageously operated with the method according to the invention; in particular, its overall efficiency can thereby be increased since the best suited controlling and/or regulating method can be respectively selected in dependence upon the rotational speed of the electric motor.

A DC motor can be activated in a particularly simple way when the first and/or second controlling and/or regulating methods are pulse width modulation (PWM) methods.

In particular, at low rotational speeds and when starting the electric motor, it is particularly expedient for the first controlling and/or regulating method to be a space vector pulse width modulation (SVPWM) method, in which all motor windings are simultaneously supplied with electric current. This method makes it possible, in particular, at low rotational speeds, to achieve an improved efficiency of the motor, since forces exerted on the rotor by the motor windings supplied with electric current in dependence upon the rotor position can be optimized in comparison with electric motors conventionally supplied with electric current.

An electric motor, which is a brushless DC motor, is preferably used. Such motors are cost-effective and maintenance-friendly.

The number of contacts on the surgical machine can be reduced when an electric motor is used, which is a sensorless electric motor. Furthermore, such motors are considerably more cost-effective to manufacture.

In accordance with a further preferred variant of the method, it may be provided that the motor comprises rotational speed detection sensors, and that the first controlling and/or regulating method is a method for controlling and/or regulating the surgical machine, in which the motor controller provides control signals for the electric motor in dependence upon an actual rotational speed determined with the rotational speed detection sensors. An actual rotational speed of the electric motor can be simply and precisely determined, in particular, at low rotational speeds, with rotational speed detection sensors.

Performance of the method becomes particularly simple when a Hall system is provided for detecting an actual rotational speed of the electric motor and when the Hall system comprises the rotational speed detection sensors. Hall systems have proven their worth in practice in a multitude of applications. In particular, Hall sensors can be made particularly small and integrated directly into the electric motor.

A rotational speed limit value between the at least one lower rotational speed range and the at least one upper rotational speed range preferably remains unaltered during operation of the machine. In this way, the method is simplified to a maximum extent.

In accordance with a further preferred variant of the method according to the invention, it may, however be provided that a rotational speed limit value between the at least one lower rotational speed range and the at least one upper rotational speed range is altered during operation of the machine. This method makes it possible to set a switchover rotational speed value in accordance with a current operating situation.

It is expedient for a switchover from the first controlling and/or regulating method to the second controlling and/or regulating method to take place at a first switchover rotational speed and for a switchover from the second controlling and/or regulating method to the first controlling and/or regulating method to take place at a second switchover rotational speed. As a result, switchover points can be set at the transition from the lower rotational speed range to the higher rotational speed range, and vice versa, in a desired manner. In particular, a frequent switching-over can thus be avoided when the machine is operating at rotational speeds in the range of the switchover rotational speed. A constant switching-over would negatively influence operation of the surgical machine, and, in particular, disturb its running smoothness.

The first switchover rotational speed is preferably equal to or greater than the second switchover rotational speed. Thus, a switchover from the low rotational speed range to the high rotational speed range preferably takes place at a higher rotational speed than vice versa.

It is advantageous for the switchover from the first controlling and/or regulating method to the second controlling and/or regulating method to take place automatically at the transition from the at least one lower rotational speed range to the at least one upper rotational speed range, or vice versa.

In this case, an operator need only specify a desired rotational speed for the surgical machine, but does not have to attend to a possible switchover between different controlling and/or regulating methods.

Performance of the method becomes particularly simple when an electric motor with three motor windings is used.

Figure 2:
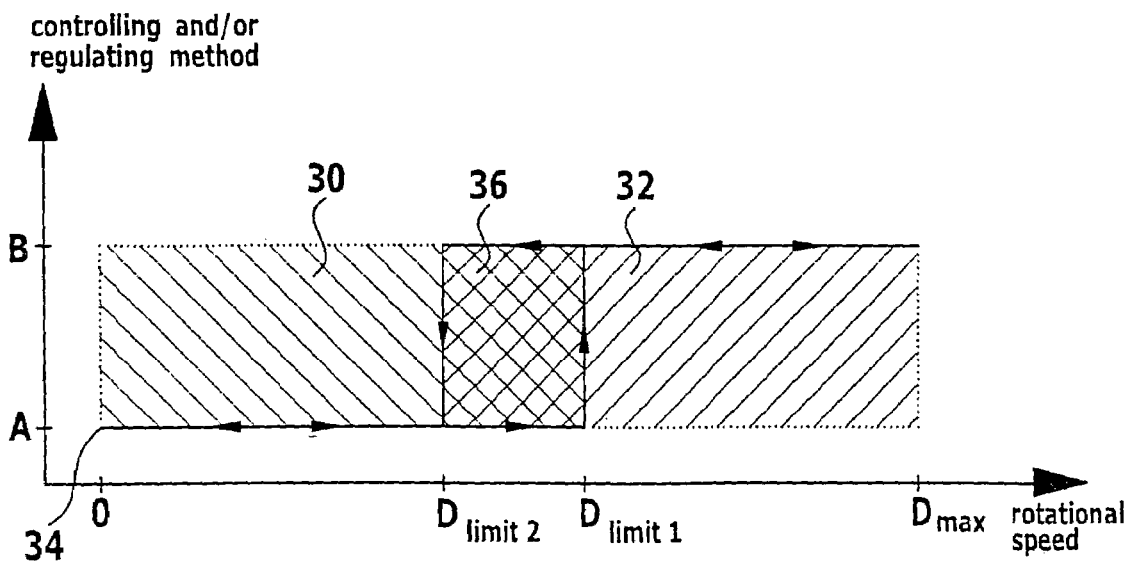
Figure 3:
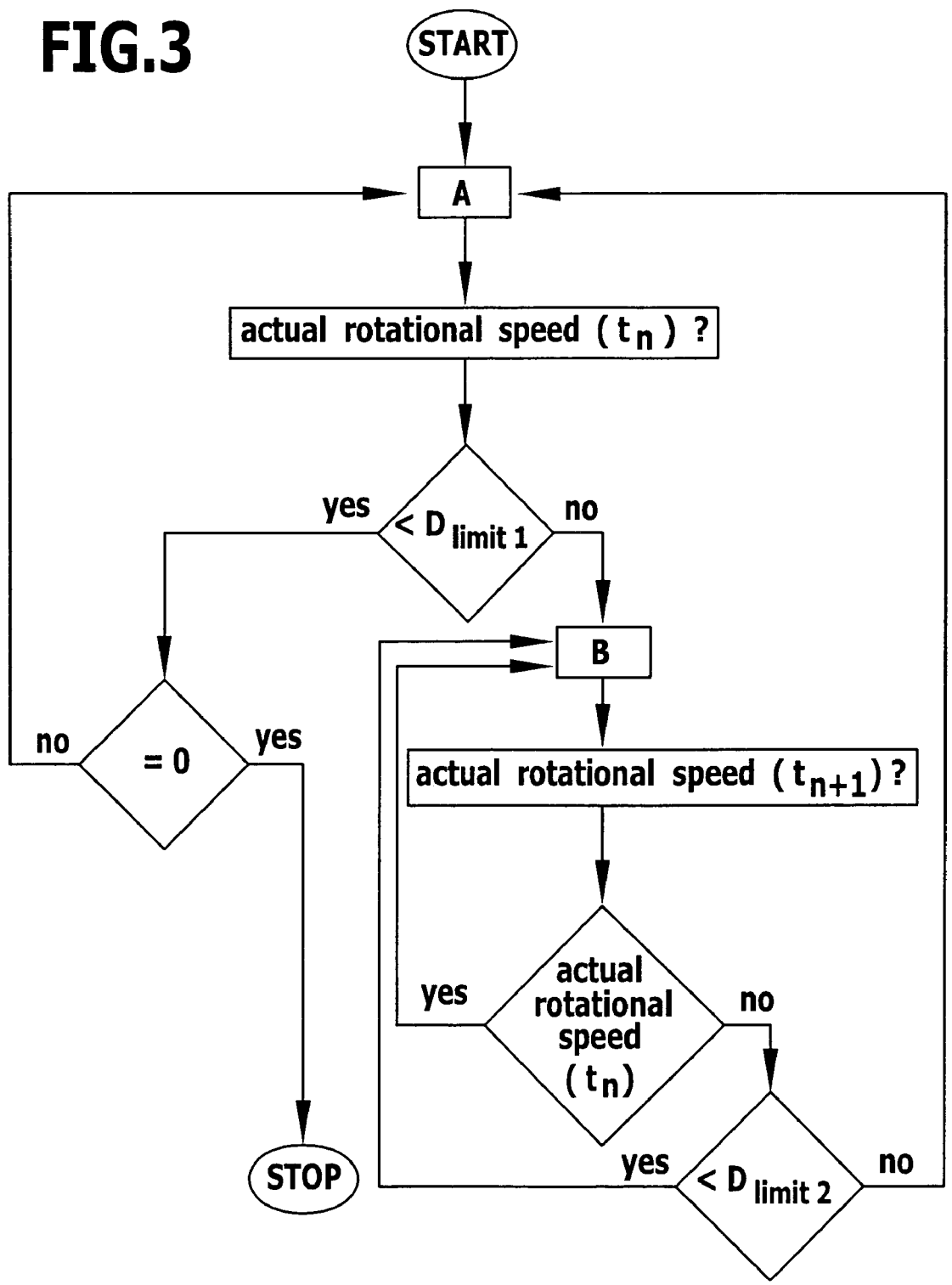

The following description of a preferred embodiment of the invention serves in conjunction with the drawings for further explanation. There are shown in:

FIG. 1: a diagrammatic representation of a surgical accumulator machine;

FIG. 2: a switching diagram of a motor controller of the accumulator machine shown in FIG. 1; and FIG. 3: a flow chart corresponding to the switching diagram in FIG. 2 for operation of the accumulator machine shown in FIG. 1.

FIG. 1 shows a surgical accumulator machine generally designated by reference numeral 10, which comprises a housing 12, in one part of which an electric motor 14, which drives a drive shaft, not shown, of the accumulator machine 10, is arranged parallel to the longitudinal axis of this housing part.

At the end of the drive shaft there is arranged a coupling 16, by means of which the accumulator machine 10 can be connected to any kind of tool, for example, drills, mills, chisels and, where necessary, by means of special couplings, also to saw blades.

A handle 18, into which a power pack 20 is insertable, protrudes transversely from the housing part of the housing 12 that receives the electric motor 14. The power pack 20 comprises a rechargeable battery 22 and a motor controller 24. A power/speed push-button 26 and an operating mode selector switch 28, which can be pressed into the handle 18 substantially parallel to a longitudinal axis of the electric motor 14, are provided for starting operation of the accumulator machine 10.

The electric motor 14 is a sensorless motor, i.e., there are no rotational speed detection sensors for detecting a rotor movement or a position of a rotor of the electric motor 14.

The motor controller 24 is so designed that a rotational speed range of the electric motor 14 is divided into two partial ranges, namely, a lower rotational speed range 30 and an upper rotational speed range 32, as shown diagrammatically in FIG. 2. Furthermore, the motor controller 24 allows two different controlling and/or regulating methods for operating the electric motor 14 to be performed. This is, firstly, a space vector pulse width modulation (SVPWM) method, which is schematically designated by A in FIGS. 2 and 3. Secondly, this is a conventional pulse width modulation (PWM) method, which is diagrammatically designated by B in FIGS. 2 and 3.

In the case of an electric motor 14 with a rotational speed detection system comprising position sensors and rotational speed detection sensors, the controlling and/or regulating method A could also be a controlling and/or regulating method in which an actual rotational speed of the electric motor 14 is determined by means of the rotational speed detection sensors and processed by the motor controller 24. In the space vector pulse width modulation (SVPWM) method and also in the conventional pulse width modulation (PWM) method an actual rotational speed of the electric motor 14 is determined by detecting the CEMF (counterelectromotive force).

The procedure when switching over from controlling and/or regulating method A to controlling and/or regulating method B will be explained in greater detail hereinbelow with reference to FIGS. 2 and 3.

The accumulator machine 10 is put into operation by an operator actuating the power/speed push-button 26. Start/stop is designated by reference numeral 34 in FIG. 2. When the operator increases the rotational speed of the electric motor 14, the motor controller 24 performs the controlling and/or regulating method A until the switchover rotational speed $D_{limit1}$ is reached. Once the switchover rotational speed $D_{limit1}$ is reached, the motor controller 24 automatically switches over to the controlling and/or regulating method B. The electric motor 14 is operated by the motor controller 24 in the controlling and/or regulating method B until the maximum rotational speed $D_{max}$ of the electric motor 14 is reached. If the rotational speed requirement for the electric motor 14 is reduced again by the operator, the controlling and/or regulating method B is still maintained for rotational speeds of the electric motor 14 that are lower than the switchover rotational speed $D_{limit1}$ until the switchover rotational speed $D_{limit2}$ is reached. Only when the switchover rotational speed $D_{limit2}$ is reached and fallen short of, does the motor controller 24 switch over to the controlling and/or regulating method A again. If the rotational speed requirement is increased again, a switchover to the controlling and/or regulating method B does, however, only take place again after the switchover rotational speed $D_{limit1}$ is exceeded.

As a result of this switching pattern, there is formed between the lower rotational speed range 30 and the upper rotational speed range 32 in FIG. 2 an overlapping range, which is designated in its entirety by reference numeral 36. In the overlapping range 36, the motor controller 24 can perform both the controlling and/or regulating method A and the controlling and/or regulating method B. Which method is carried out, will depend on whether the rotational speed requirement is increased from an actual rotational speed below the switchover rotational speed $D_{limit2}$ or is lowered from above the switchover rotational speed $D_{limit1}$. All in all, this results in the hysteresis-like curve shown in FIG. 2, on which it is possible to move around the overlapping range 36 in the counter-clockwise direction.

The mode of operation of the motor controller 24 for switching over between the two controlling and/or regulating methods A and B will become apparent from FIG. 3. The starting point is an electric motor 14 at a standstill. When it is started, the motor controller 24 carries out the controlling and/or regulating method A. The actual rotational speed at the point in time $t_n$ is determined at periodic intervals. After determining the actual rotational speed at the point in time $t_n$, it is inquired whether the actual rotational speed is less than the switchover rotational speed $D_{limit1}$. If the rotational speed is less than the switchover rotational speed $D_{limit1}$, it is then inquired whether the rotational speed is equal to 0. If this is the case, the motor controller 24 then stops operation of the electric motor 14. If the actual rotational speed is less than the switchover rotational speed $D_{limit1}$, but greater than 0, the controlling and/or regulating method A is then carried out further.

If the actual rotational speed determined at the point in time $t_n$ is greater than the switchover rotational speed $D_{limit1}$, the motor controller 24 then switches over to the controlling and/or regulating method B. The actual rotational speed at the point in time $t_{n+1}$ is kept on being determined at periodic intervals and subsequently compared with the previously determined actual rotational speed at the point in time $t_n$. If the actual rotational speed at the point in time $t_{n+1}$ is greater than the actual rotational speed at the point in time $t_n$, the motor controller 24 then continues to carry out the controlling and/or regulating method B. If, however, the actual rotational speed at the point in time $t_{n+1}$ is less than the actual rotational speed at the point in time $t_n$, the actual rotational speed is then compared with the switchover rotational speed $D_{limit2}$. If the actual rotational speed is greater than the switchover rotational speed $D_{limit2}$, the motor controller then continues to carry out the controlling and/or regulating method B. Otherwise the motor controller 24 automatically switches over to the controlling and/or regulating method A.

The switchover between the two controlling and/or regulating methods A and B has, in particular, the advantage that a space vector pulse width modulation (SVPWM) method carried out at low rotational speeds, which shows undesired damping effects at high rotational speeds, which result in motor losses and a negative influence on the efficiency of the accumulator machine 10, need not be used at high rotational speeds.

Hardware- or software-based implementation of the two controlling and/or regulating methods A and B in the motor controller is possible.

The invention claimed is:

1. Surgical machine comprising:
    a battery driven electric motor comprising a rotor and at least two motor windings,
    a battery for driving the electric motor, and
    a motor controller for at least one of controlling and regulating the electric motor, wherein:
    an entire rotational speed range of the surgical machine is divided into at least one lower rotational speed range for low rotational speeds and at least one upper rotational speed range for higher rotational speeds than the speeds in the at least one lower rotational speed range,
    the motor controller is adapted so that a first method (A) for said at least one of controlling and regulating the electric motor is performable in the at least one lower rotational speed range, and a second method (B) for said at least one of controlling and regulating the electric motor is performable in the at least one upper rotational speed range, and
    the first method (A) comprises a space vector pulse width modulation (SVPWM) method in which all motor windings are able to be simultaneously supplied with electric current.

2. Machine in accordance with claim 1, wherein the second method (B) is a pulse width modulation (PWM) method.

3. Machine in accordance with claim 1, wherein the electric motor is a brushless DC motor.

4. Machine in accordance with claim 1, wherein the electric motor is a sensorless electric motor.

5. Machine in accordance with claim 1, wherein:
    the electric motor further comprises rotational speed detection sensors, and
    the motor controller is adapted so that the first method (A) is a method for said at least one of controlling and regulating the surgical machine in which the motor controller provides control signals for the electric motor in dependence upon an actual rotational speed determined with the rotational speed detection sensors.

6. Machine in accordance with claim 5, wherein a Hall system is provided for detecting the actual rotational speed of the electric motor, and the Hall system comprises the rotational speed detection sensors.

7. Machine in accordance with claim 1, wherein a rotational speed limit value ($D_{limit1}$, $D_{limit2}$) between the at least one lower rotational speed range and the at least one upper rotational speed range is unalterable.

8. Machine in accordance with claim 1, wherein a rotational speed limit value ($D_{limit1}$, $D_{limit2}$) between the at least one lower rotational speed range and the at least one upper rotational speed range is alterable.

9. Machine in accordance with claim 1, wherein the motor controller is adapted so that a switchover from the first method (A) to the second method (B) takes place at a first switchover rotational speed ($D_{limit1}$), and a switchover from the second method (B) to the first method (A) takes place at a second switchover rotational speed ($D_{limit2}$).

10. Machine in accordance with claim 9, wherein the first switchover rotational speed ($D_{limit1}$) is equal to or greater than the second switchover rotational speed ($D_{limit2}$).

11. Machine in accordance with claim 1, wherein the motor controller is adapted so that the switchover from the first method (A) to the second method (B) takes place automatically at the transition from the at least one lower rotational speed range to the at least one upper rotational speed range, and vice versa.

12. Machine in accordance with claim 1, wherein the electric motor comprises three motor windings.

13. Method for operating a surgical machine with a battery driven electric motor comprising a rotor and at least two motor windings, a battery for driving the electric motor, and with a motor controller for at least one of controlling and regulating the electric motor, said method comprising:
    dividing the entire rotational speed range of the surgical machine into at least one lower rotational speed range for low rotational speeds and at least one upper rotational speed range for higher rotational speeds than those in the at least one lower rotational speed range,
    performing a first method for said at least one of controlling and regulating the electric motor in the at least one lower rotational speed range, and
    performing a second method for said at least one of controlling and regulating the electric motor in the at least one upper rotational speed range;
    wherein the first method is a space vector pulse width modulation (SVPWM) method, in which all motor windings are simultaneously supplied with electric current.

14. Method in accordance with claim 13, wherein the second method is a pulse width modulation (PWM) method.

15. Method in accordance with claim 13, wherein an electric motor, which is a brushless DC motor, is used.

16. Method in accordance with claim 13, wherein an electric motor, which is a sensorless electric motor, is used.

17. Method in accordance with claim 13, wherein:
the motor further comprises rotational speed detection sensors, and
the first method is a method for said at least one of controlling and regulating the surgical machine in which the motor controller provides control signals for the electric motor in dependence upon an actual rotational speed determined with the rotational speed detection sensors.

18. Method in accordance with claim 17, wherein a Hall system is provided for detecting the actual rotational speed of the electric motor, and the Hall system comprises the rotational speed detection sensors.

19. Method in accordance with claim 13, wherein a rotational speed limit value between the at least one lower rotational speed range and the at least one upper rotational speed range remains unaltered during operation of the machine.

20. Method in accordance with claim 13, wherein a rotational speed limit value between the at least one lower rotational speed range and the at least one upper rotational speed range is altered during operation of the machine.

21. Method in accordance with claim 13, wherein a switchover from the first method to the second method takes place at a first switchover rotational speed, and a switchover from the second method to the first method takes place at a second switchover rotational speed.

22. Method in accordance with claim 21, wherein the first switchover rotational speed is equal to or greater than the second switchover rotational speed.

23. Method in accordance with claim 13, wherein the switchover from the first method to the second method takes place automatically at the transition from the at least one lower rotational speed range to the at least one upper rotational speed range, and vice versa.

24. Method in accordance with claim 13, wherein an electric motor with three motor windings is used.

* * * * *